United States Patent [19]

Zobel

[11] 4,149,769

[45] Apr. 17, 1979

[54] ENDOSCOPE TELESCOPES WITH TUBULAR CONNECTED OCULAR AND OBJECTIVE LENS MEANS

[75] Inventor: Jürgen Zobel, Knittlingen, Fed. Rep. of Germany

[73] Assignee: Richard Wolf GmbH, Knittlingen, Fed. Rep. of Germany

[21] Appl. No.: 835,036

[22] Filed: Sep. 20, 1977

[51] Int. Cl.² .............................................. G02B 7/04
[52] U.S. Cl. ....................................... 350/43; 350/44
[58] Field of Search .................................. 350/40–44, 350/54, 187, 186, 79, 78; 128/4

[56] References Cited

U.S. PATENT DOCUMENTS

| | | | |
|---|---|---|---|
| 2,454,686 | 11/1948 | Back | 350/40 |
| 2,804,802 | 9/1957 | Loeck | 350/54 |
| 3,094,581 | 6/1963 | Back | 350/186 |
| 3,178,994 | 4/1965 | Lang | 350/42 |
| 3,433,559 | 3/1969 | Vockenhuber et al. | 350/42 |
| 3,608,998 | 9/1971 | Rinker | 350/42 |

FOREIGN PATENT DOCUMENTS 4063 of 1905 United Kingdom ...................... 350/44

Primary Examiner—Jon W. Henry
Attorney, Agent, or Firm—Kinzer, Plyer, Dorn & McEachran

[57] ABSTRACT

An endoscope telescope comprising first and second telescopically mounted tubular members of which the second tubular member is mounted in said first tubular member for movement relative thereto, at least two objective lens means and at least two ocular lens means of which the most distal objective lens means and the most distal ocular lens means are positioned in said first tubular member and the most proximal objective lens means and most proximal ocular lens means are positioned in said second tubular member, and an image transmitting system arranged in said second tubular member between the most proximal objective lens means and the most distal ocular lens means.

2 Claims, 2 Drawing Figures

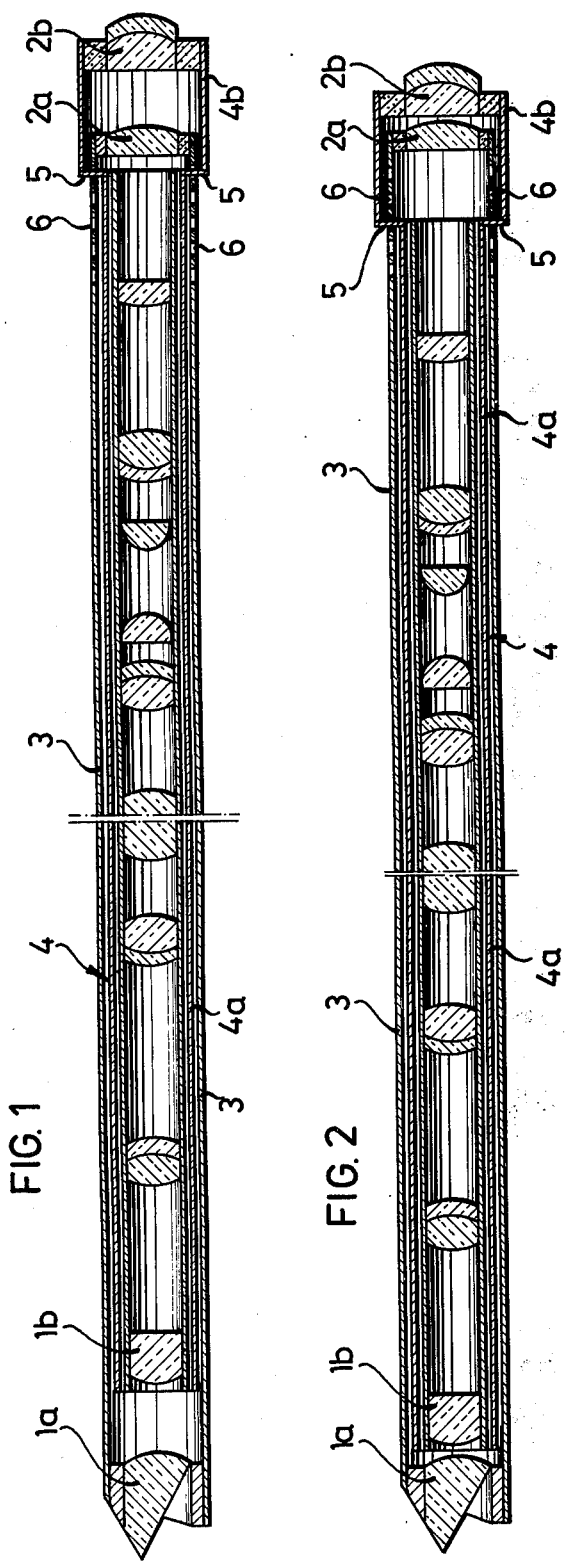

ENDOSCOPE TELESCOPES WITH TUBULAR CONNECTED OCULAR AND OBJECTIVE LENS MEANS

BACKGROUND OF THE INVENTION

1. Field of the Invention

The invention relates to an endoscope telescope having an objective lens-system of adjustable focal length and an optical image-transmitting system which follows on from the objective lens-system and which terminates at a proximal ocular or eye piece lens. Hereinafter such an endoscope telescope will be referred to as an endoscope telescope of the kind described.

2. Description of the Prior Art

In the case of an endoscopic viewing tube it is known from German patent specification No. 1,234,920 to associate a rod-like fibre image-conductor, in a tubular envelope, with an adjustable objective which can be adjusted longitudinally in relation to the image-conductor so that in this way, if the distance between the objective and the object viewed alters, as a result of movement of the image-conductor the image can be re-focussed onto the distal terminal face of the image-conductor, which allows an adjustment to be made for sharpness when the distance to the object viewed changes. On the other hand, for the doctor performing the examination it is of advantage if it is possible for him to alter the scale to which the distance from the object to the objective remains the same. In this way the doctor can always work with the objective sufficiently far away from the object, so that there is no possibility of damage being done in the body cavity. An endoscope telescope for this purpose has already been disclosed in German Auslegeschrift No. 1,766,695 in which the objective consists of two collecting lenses or two groups of lenses which can be moved in unison towards or away from one or another from the proximal end by means of wires or the like, so that on the one hand the scale of reproduction can be altered and on the other hand the image always remains trained on the distal end of the fibre image-conductor. This joint control of the two objective collecting lenses calls for a complicated mechanical arrangement in the telescope tube and for the passage of control wires, with the increase in the diameter of the telescope which this makes necessary. In the case of the adjustable endoscope disclosed in German Pat. No. 1,566,112 the exit pupil alters with enlargement, meaning that the exit pupil is reduced to approximately the same degree as enlargement increases, so that there is then insufficient light available for the taking of photographs or films.

Therefore, it is an object of the invention, where there is a facility for altering the scale of reproduction while the distance to the object viewed remains the same, to compensate, in a simple fashion and while maintaining the image brightness or exit pupil approximately constant, for the movement of the point of focus and thus of the position of the image which occurs when the focal length of the object is altered.

SUMMARY OF THE INVENTION

In an endoscope telescope of the kind described, this object is achieved in accordance with the invention by having not only the variable focus objective but also the ocular consists of two lenses or groups of lenses, of which the distal objective lens and the more distal ocular lens are positioned in an envelope tube and the more proximal objective lens and the more proximal ocular lens, together with an image transmitting lens-system situated between the more distal ocular lens and the more proximal objective lens, are arranged in an optical system tube which can be moved longitudinally in relation to the envelope tube.

By this means it becomes possible, while the distance from the objective to the object viewed remains the same, to achieve the required enlargement of the image of the object simply by moving the envelope tube in relation to the optical system tube. When this is done the mispositioning of the image which occurs at the objective end is compensated for at the ocular end, the important thing in this case being that the exit pupil remains approximately constant since when the focal length of the objective is altered the focal length of the ocular changes only slightly or not at all. At the same time the image of the object is transmitted to the ocular through the lens system of the optical system tube, i.e. it is no longer necessary to train the image in known fashion exactly onto the end of a fibre-image conductor of a known kind by means of the objective.

BRIEF DESCRIPTION OF THE DRAWINGS

FIGS. 1 and 2 are longitudinal sections through an endoscope telescope constructed according to the invention, showing the objective and ocular lenses in two different terminal positions respectively.

DESCRIPTION OF THE PREFERRED EMBODIMENT

In the embodiment shown in the drawings the objective of the endoscope telescope consists of two separate lenses 1a and 1b or of two separate groups of lenses, which the lenses 1a and 1b can be taken diagrammatically to represent, and the ocular consists of two separate lenses 2a and 2b, i.e. condensing lens 2a and an achromatic lens 2b or groups of lenses which the lenses 2a and 2b can be taken diagrammatically to represent. The more distal objective lens 1a and the more distal ocular lens 2a are arranged in the ends of an envelope tube 3.

The more proximal objective lens 1b and the more proximal ocular lens 2b are arranged in the ends of an optical system tube 4 which also contains the lens system which transmits the image, this lens system being situated between the more proximal objective lens 1b and the more distal ocular lens 2a. The optical system tube 4 consists of a section 4a which extends through the envelope tube 3 and of a proximal section 4b which holds the more proximal ocular lens 2b and which is of larger diameter than the envelope tube 3. Section 4a is connected to section 4b by pins 5 or bridges which pass through longitudinal slots 6 in the envelope tube 3. The possibility also exists however of connecting the more proximal ocular lens to section 4a of the optical system tube by a linkage.

If the tubular member 4 is moved in relation to the tubular member 3 while the distance from the objective lens 1a to the object remains constant, the focal length of the two-part objective 1a, 1b, and thus the enlargement of the image of the object, alters, while the focal length of the two-part ocular 2a, 2b changes only slightly, the error at the objective end, namely the change in the position of the image, being compensated for at the ocular end without the exit pupil changing to any substantial degree when the image is enlarged, i.e. the brightness of the image is not affected.

I claim

1. An endoscope telescope having proximal and distal ends and comprising:
   (a) a first tubular member,
   (b) a second tubular member telescopically mounted in said first tubular member,
   (c) an objective lens-system of adjustable focal length comprising at least two objective lens means each having at least one objective lens,
   (d) the most distal of said objective lens means being positioned in said first tubular member and the most proximal of said objective lens means being positioned in said second tubular member,
   (e) at least two ocular lens means each having at least one ocular lens,
   (f) the most distal of said ocular lens means being positioned in said first tubular member, and the most proximal of said ocular lens means being positioned in said second tubular member,
   (g) an optical image-transmitting system arranged in said second tubular member between said most distal ocular lens means and said most proximal objective lens means, and
   (h) means mounting said first and second tubular members for movement of said second tubular member relative to said first tubular member.

2. An endoscope telescope according to claim 1, wherein said first tubular member defines at least one longitudinal slot at a location distally of its proximal end and distally of said most distal ocular lens means and wherein said means mounting said second tubular member for relative movement comprises projection means which passes through said at least one slot and which is connected to said second tubular member in a section thereof which extends through said first tubular member and which is connected to a section of said second tubular member which mounts said most proximal ocular lens means and which is wider than said first tubular member.

* * * * *